United States Patent [19]

Daley

[11] 4,324,460
[45] Apr. 13, 1982

[54] METHOD AND APPARATUS FOR TESTING FLICKER FUSION FREQUENCY

[76] Inventor: Michael L. Daley, 9345 SW. Westhaven Dr., Portland, Oreg. 97225

[21] Appl. No.: 141,303

[22] Filed: Apr. 18, 1980

[51] Int. Cl.³ .......................... A61B 3/02; A61B 3/00
[52] U.S. Cl. ......................................... 351/36; 351/39
[58] Field of Search .................................. 351/36, 39

[56] References Cited
U.S. PATENT DOCUMENTS 3,424,519  1/1969  White ..................................... 351/36
3,814,510  6/1974  Adler et al. ........................... 351/36

Primary Examiner—John K. Corbin
Assistant Examiner—Rodney Bovernick
Attorney, Agent, or Firm—Kolisch, Hartwell & Dickinson

[57] ABSTRACT

Apparatus for testing temporal vision including a target light produced on a portion of a viewing area. A boundary is provided between the target light and a background light, such being produced on substantially all of the viewing area. A first oscillator switches the target light on and off while a second oscillator is available to switch the background light on and off. A frequency control is provided to vary the rate of switching of the target light.

4 Claims, 6 Drawing Figures

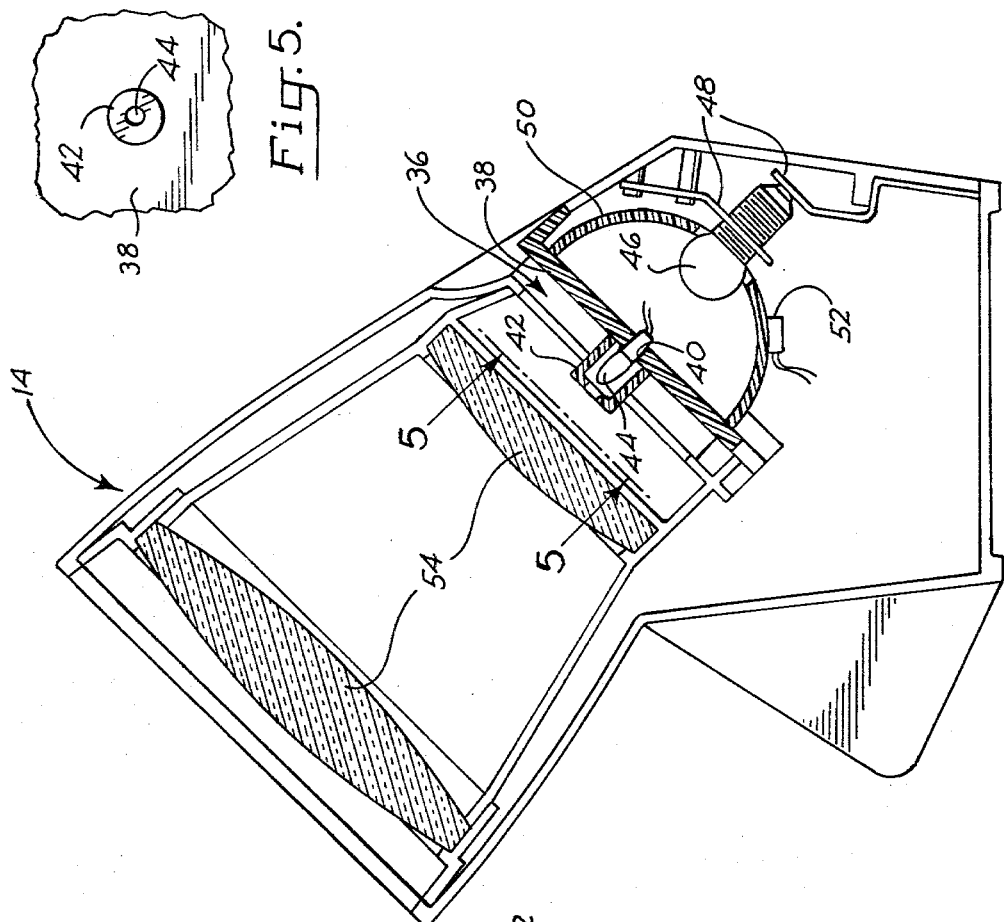
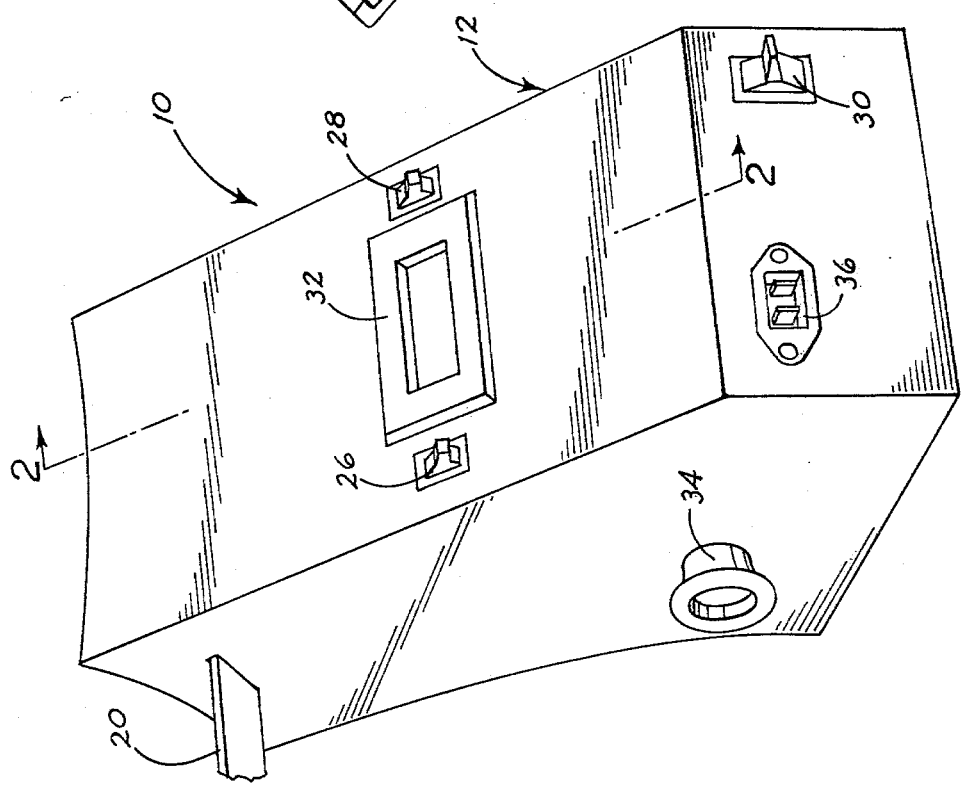

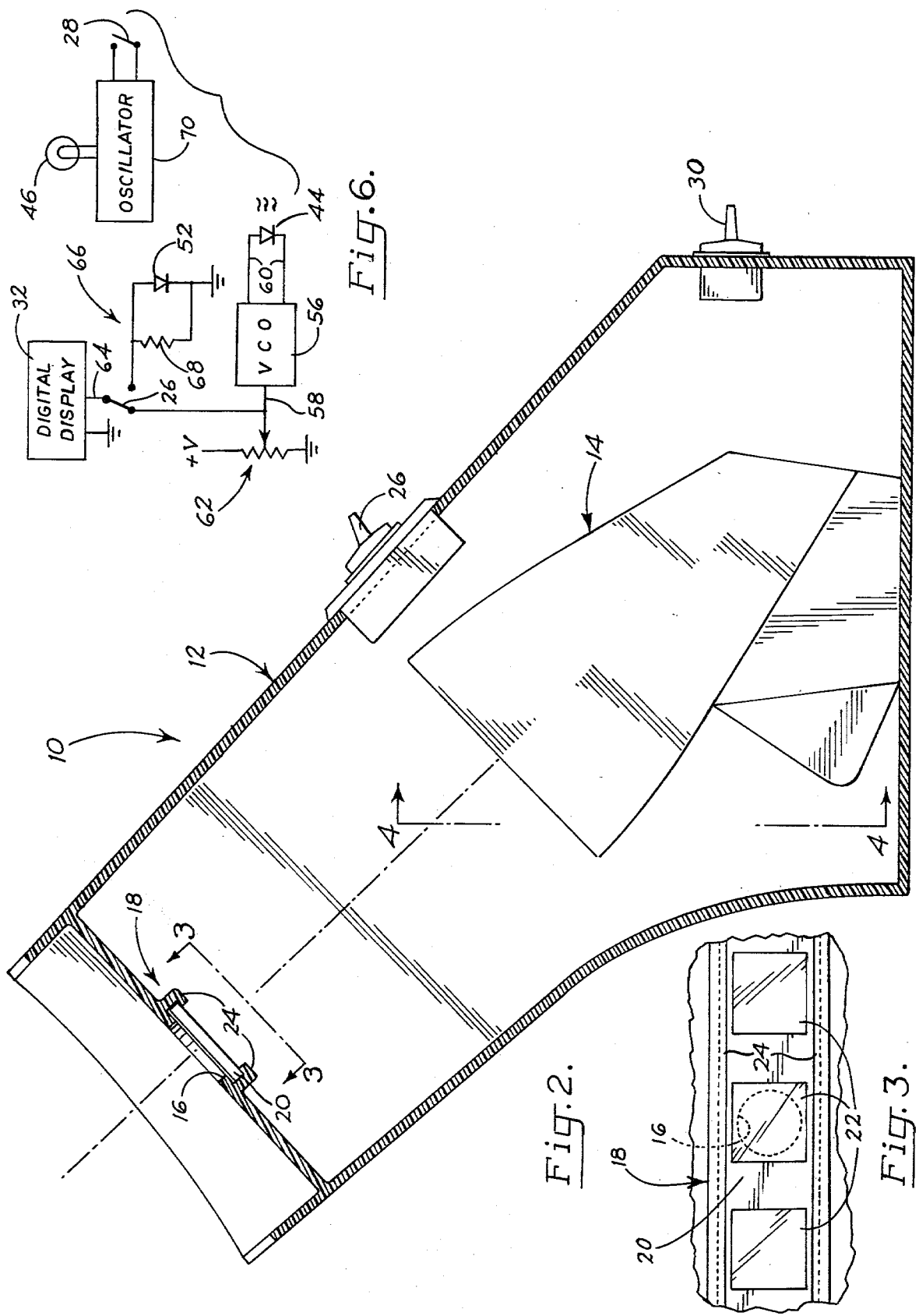

METHOD AND APPARATUS FOR TESTING FLICKER FUSION FREQUENCY

BACKGROUND AND SUMMARY OF THE INVENTION

This invention pertains to a method and apparatus for determining a person's flicker fusion threshold. When a person observes light pulses which are increasing in frequency, at some point it appears to the person that he is observing a continuous light. That point is known as the flicker fusion threshold. The instant method and apparatus provides such varying light pulses in the presence of either continuous or flickering background light. By so doing, with the latter method, the incidence of detection of abnormal flicker fusion thresholds in persons having neurological deterioration of their optic pathways is increased.

In the past, apparatus for detecting the flicker fusion threshold or critical flicker fusion (CFF) frequency as it is known, included only a flickering target light, the frequency of which is adjustable. Typically, a person being tested increases the frequency of the flickering target light to the point at which it appears to be continuous, such frequency being that person's CFF frequency.

The instant invention includes means for providing a flashing background light in the presence of the flickering target light. The person being tested increases the frequency of the target light to the point where it appears as if a non-flickering light. The frequency of flickering at that point is referred to herein as the incremental critical flicker fusion (ICFF) frequency.

It is well known that several diseases, i.e., multiple sclerosis, diabetes and glaucoma involve neurological deterioration. Such deterioration can be detected and the status of neurological function can be monitored by use of both the CFF and ICFF test. As a disease having neurological involvement with the optic pathways becomes more severe, both the CFF and ICFF for that person decreases.

Another past apparatus for measuring CFF frequency includes a central flickering light surrounded by a steady background light, both of such lights being covered by an opal glass which diffuses the boundary between the two lights. The central flickering light is varied (as in past apparatus with a single flickering light) to the point at which the person being tested observes what appears to be a continuous light.

A general object of the present invention is to provide both an improved and a unique method and apparaus for obtaining fusion threshold measures.

A related object is to provide improved detection of visual disfunction.

According to a preferred embodiment of the invention, a translucent viewing panel is provided, such having a white incandescent background light mounted behind it. A red light-emitting diode is mounted on the front of the screen in the center of an opaque cylinder which encloses the diode. The cylinder is mounted on the viewing panel. The diode's leads pass through a small hole in the panel and are connected to a voltage-controlled oscillator. The background light is connected to either a different oscillator, such switching the background light on and off at a frequency of 10 cycles per second or to a continuous power source. A pair of lenses positioned in front of the viewing panel focus the exiting light into parallel rays. A hood is provided to exclude all other light from the viewing panel. Additionally, the hood is provided with an aperture into which a test subject views the panel. Also provided are colored filters positionable between the aperture and the viewing screen for selectively varying the light entering the eye, and, accordingly, varying the population of fibers within the retina which react to the light.

A potentiometer varies the frequency of the voltage-controlled oscillator and accordingly varies the frequency of flashing of the light-emitting diode. A digital display indicates the frequency at which the light-emitting diode flashes. The test subject increases the frequency to the point at which the light-emitting diode appears to be on continuously; the frequency displayed at that point is the fusion threshold frequency for which the instant apparatus is constructed to detect. For the instant apparatus, the above-described measurement is called the incremental critical flicker fusion (ICFF) frequency (or threshold).

Other features and advantages offered by the invention will become more fully apparent as the description which follows is read in conjunction with the accompanying drawings.

DESCRIPTION OF THE DRAWINGS

FIG. 1 is a perspective view of the instant embodiment of the invention.

FIG. 2 is a partial cross-sectional view taken along line 2—2 in FIG. 1.

FIG. 3 is a partial view taken along the lines 3—3 in FIG. 2.

FIG. 4 is an enlarged cross-sectional view taken along line 4—4 in FIG. 2.

FIG. 5 is a partial view along line 5—5 in FIG. 3.

FIG. 6 is a schematic diagram of a portion of the instant embodiment of the invention.

DETAILED DESCRIPTION

Turning now to the drawings, indicated generally at 10 in FIG. 1 is a preferred embodiment of the apparatus of the invention. Looking now to FIG. 2, the preferred embodiment is shown with a portion thereof in cross-section. A hood 12 (shown in cross section) encloses a viewer 14 (shown in complete side elevation). Viewer 14, in the instant embodiment of the invention, is a conventional lighted slide viewer having certain modifications which will hereinafter be described. Included within hood 12 is a round aperture 16. Positioned adjacent aperture 16 intermediate the aperture and the viewer is filter carrier 18. As can best be seen in FIG. 3, the filter carrier includes a frame 20, such supporting different colored filters 22 at spaced intervals along the length of frame 20. Frame 20 is slidably constrained within guides 24, thus allowing frame 20 to be selectively positioned, with respect to aperture 16, along its length. As can be seen in FIG. 1, one end of frame 20 extends from a slot in hood 12 to allow selection of a certain one of filters 22 to be positioned between the aperture and the viewer, or alternatively, to allow removal of the frame to eliminate filtration between the aperture and the viewer.

Also included on hood 12 are control switches 26, 28, 30, digital display 32, control knob 34 and power connection 36, the functioning of which will be later described.

Speaking now only in general terms, when it is desired to obtain a flicker fusion measurement using the instant apparatus, a subject observes viewer 14 with one eye through aperture 16. As will be more fully described, the subject observes either a flickering background (such flickering at 10 cycles per second) or a nonflickering background, and a flickering red target light centered against the background. The subject turns knob 34, thus increasing the frequency of the flickering target light. Display 32 indicates the frequency at which the target light is flashing. The subject increases the frequency of flashing of the target light using knob 34 until the target light appears to be continuously lighted (i.e., no flickering). The subject stops turning knob 34 at that point and the frequency on display 32 is what is referred to herein as the incremental critical flicker fusion (ICFF) frequency for the subject, when the background is flickering. When the background is either off or steadily lit, the measurement taken is the CFF frequency.

Looking now to FIG. 4 for a more detailed examination of the construction of viewer 14, indicated generally at 36 is a viewing area. Included within the viewing area is a white translucent panel 38. In the instant embodiment of the invention, panel 38 has an aperture 40 located at its approximate center. A collar 42, also referred to herein as target-defining means, is mounted on panel 38 over aperture 40. The collar is cylindrical in shape and has a bore centered along its axis passing therethrough. A red light-emitting diode 44 is positioned within the bore of the collar as shown. The leads of the diode pass through the aperture to circuitry (not shown in FIG. 4), such circuitry being later described herein.

Centered behind panel 38 is an incandescent light 46, such also being referred to herein as background light producing means. Light 46 is mounted on electrical contacts 48 which are connected to the above-mentioned circuitry. A relatively opaque reflector 50 (shown in cross section in FIG. 4) encloses the bulb of light 46 thus allowing most of the light from the bulb to be emitted only through panel 38.

A photodiode 52 having a pair of leads is mounted on the exterior of reflector 50 adjacent light 46. When light passes through reflector 50 and strikes the photodiode, a potential difference is generated between its leads. The leads of photodiode 52 are likewise connected to the circuitry.

A pair of conventional lenses 54 are centered over panel 38 and are securely mounted as shown. Light rays which leave viewer 14 are focused by lens pair 54 so that the exiting light rays are parallel one to another.

In FIG. 6, a schematic diagram illustrates the interconnection of some of the previously-described structure, such being shown schematically in FIG. 6 with the same number which has been previously used for identification. Conventional power connections have been omitted. Also included in FIG. 6 is a voltage-controlled oscillator 56 or first oscillator means. Such is of conventional structure and operation and in the instant embodiment of the invention an AD 537 integrated circuit manufactured by Analog Devices is used. Oscillator 56 has an input terminal 58 and a pair of output terminals 60. Oscillator 56 operates in a conventional manner and produces a square wave on its output terminals 60, such being applied across the lead of light-emitting diode 44. As a DC voltage on terminal 58 is increased, the frequency of the square wave on terminal 60 likewise increases. The square wave maintains a 50 percent duty cycle.

A variable potentiometer 62 has a positive source of voltage applied thereto, the wiper arm of the potentiometer being applied to input terminal 58 of the voltage-controlled oscillator. Potentiometer 62 is varied by turning knob 34 (in FIG. 1).

Digital display 32 (shown only schematically in FIG. 6) is of conventional construction and has one input terminal 64. A voltage level appearing on terminal 64 is processed by circuitry within display 32 which generates an output, such being a display of a decimal number between 0 and 99.9 in 1/10th increments. The value of the number appearing on the display is proportional to the magnitude of the voltage appearing at terminal 64.

Switch 26 is a single pole double throw switch which serves to apply either the voltage on the wiper arm of potentiometer 62 or a voltage generated by calibration-check circuitry 66 to the input of the digital display. Included within circuitry 66 is the previously-described photodiode 52, such having its leads applied across a resistor 68.

A conventional oscillator 70 applies a 10 cycle per second, 50 percent duty cycle, square wave to light 46. Switch 28 changes the oscillator output to a steady state DC voltage. Thus, when switch 28 is open as shown in FIG. 5, light 46 is turning on and off at the rate of 10 cycles per second. When switch 28 is closed, light 46 remains continuously lit.

In operation of apparatus 10, prior to testing a subject with the apparatus, a calibration check is performed to assure that the light emitted from light 46 has not varied from prior tests. Accordingly, switch 26 is switched from the position shown in FIG. 6 to its other position, thus providing digital display 32 with an input from calibration-check circuitry 66. With switch 28 in the position illustrated in FIG. 6, oscillator 70 drives light 46 on and off at 10 cycles per second at a 50 percent duty cycle, i.e., the light is on half the time and off half the time. The output of light 46 shines on photodiode 52 and generates a current proportional to the amount of light emitted. Such current travels through resistor 68 and a voltage is thus applied to the input of display 32. The number generated by the display corresponds to the intensity of light 46. The present display value is compared with numbers so generated in the past to assure that there has been no drop off of light intensity. Next, switch 28 is closed thus causing oscillator 70 to drive light 46 continuously. A second higher reading is generated on digital display 32 and this reading is also compared with readings taken in the past (with switch 28 closed) to assure no drop off in steady state operation of light 46. Once it is determined that the output of light 46 is consistent with past uses of the apparatus, the test to determine either a subject's CFF or ICFF threshold can proceed.

To set apparatus 10 for testing a subject's ICFF frequency, switches 26, 28 are positioned as shown in FIG. 6. Knob 34 is turned to adjust potentiometer 62 so that light-emitting diode 44 is flashing at a frequency of between 5 and 15 cycles per second. As will be recalled, digital display 32 displays the frequency at which diode 44 flashes. Frame 20 is moved to position a selected filter 22 adjacent aperture 16, although for the present example let us assume that carrier 18 is removed.

The subject positions one eye in front of aperture 16 and observes the viewing area. The subject sees essentially the view of FIG. 5. With light 46 flashing at 10 cycles per second, panel 38 emits a diffused even-intensity light over its surface, such flashing at the rate of 10 cycles per second. Diode 44 is emitting a red flashing light at the rate selected by adjustment of knob 34. Collar 42 provides a distinct separation between the target light and the background light.

The subject adjusts knob 34, thus increasing the voltage applied to oscillator 56 and correspondingly, the rate of flashing of diode 44. At some point, during the adjustment of knob 34, diode 44 appears to the subject as if continuously lit. The subject stops adjustment of the knob at that point. The frequency of the flashing as indicated by display 32 is then recorded and is known as the subject's incremental critical flicker fusion frequency.

It has been found that the continuously flashing background light provides increased abnormal responses in subjects having diseases with neurological involvement compared to responses obtained with past apparatus. The flashing background light serves to stimulate and excite communication between neurons affected by the flashing light. The pressure of certain diseases serve to disrupt neural communication during an excited phase and accordingly, the disruption is reflected in a lower than average ICFF threshold for a subject with optic pathway involvement.

When the above-described procedure is followed with switch 28 closed, a subject's CFF threshold is determined. Although past apparatus exist for determining the CFF threshold, they either do not include a background light or they provide no boundary between the background and target lights. Collar 42 provides a distinct boundary between the target light and the background light thus allowing an accurate determination of the CFF threshold.

The target-defining means (collar 42 in the instant embodiment of the invention) serves to separate the flashing target light from the flashing background light. Such separation is important so that the subject can clearly observe the flashing target light as it approaches his ICFF frequency. In the instant embodiment of the invention, light 46 emits a white light. However, it is to be appreciated that various combinations of colors of background light, target light, and filtration light can be selected to alter the resultant neural stimulation as a subject observes the viewing area. For example, it has been found that the complications of diabetes causes a neurological involvement, such being most readily detectable by use of a blue filter adjacent aperture 16.

In the instant embodiment of the invention hood 12 serves several purposes. Aperture 16 allows for only monocular viewing by a subject. Additionally, hood 12 serves to block light from a subject's eyes other than that emitting from viewer 14. Finally, the distance between the source of viewer light and a patients eye is standardized so that for different tests (or for different subjects) the light of both the target light and background light subtend the same area in the subjects eye.

In the instant embodiment of the invention, successful results have been obtained by using a background light which generates a mean luminence of approximately 10 to 20 millilamberts at aperture 16. Likewise, a luminance of approximately 50 millilamberts for the target light (also measured at aperture 16) was found to produce useful test results.

Although a preferred embodiment of the invention has been described, it is to be appreciated that variations and modifications may be made without departing from the spirit of the invention.

It is claimed and desired to secure by Letters Patent:

1. Apparatus for testing temporal vision comprising,
   a viewing area,
   means for producing a target light on a portion of said area,
   means for producing background light on substantially all of said area,
   target-defining means for defining a boundary which provides a viewably distinct separation between said target light and said background light,
   first oscillator means operatively connected to said target-light producing means, said oscillator means being operative to switch said target light between a condition of full illumination and a condition of no illumination,
   second oscillator means operatively connected to said background-light producing means, said second oscillator means being operative to switch said background light between a condition of full illumination and a condition of no illumination, and
   a frequency control, operatively connected to said first oscillator means, operative to selectively vary the rate of switching of said target light.

2. The apparatus of claim 1 which further includes means for positioning a colored filter in the path of such person's view.

3. A method for testing a person's temporal vision comprising the steps of,
   producing a target light on a portion of a viewing area viewed by the person,
   producing a background light on substantially all of said area,
   providing a defined boundary for creating a viewably distinct separation between said target light and said background light,
   switching said target light between a condition of full illumination and a condition of no illumination,
   switching said background light between a condition of full illumination and a condition of no illumination, and
   varying the rate of switching of said target light.

4. The method of claim 3 which further includes the step of positioning a colored filter in the path of such person's view.

* * * * *